United States Patent [19]

Meyer et al.

[11] 4,022,898
[45] May 10, 1977

[54] 2-AMINO-4-PYRIMIDYL-1,4-DIHYDROPYRIDINE DERIVATIVES

[75] Inventors: Horst Meyer, Wuppertal; Friedrich Bossert, Wuppertal-Elberfeld; Wulf Vater, Opladen; Kurt Stoepel, Wuppertal, all of Germany

[73] Assignee: Bayer Aktiengesellschaft, Germany

[22] Filed: May 7, 1975

[21] Appl. No.: 575,369

Related U.S. Application Data

[62] Division of Ser. No. 438,603, Feb. 1, 1974, Pat. No. 3,929,798, which is a division of Ser. No. 336,639, Feb. 28, 1973, Pat. No. 3,867,393.

[30] Foreign Application Priority Data

Sept. 12, 1972 Germany ............... 2210674

[52] U.S. Cl. ............... 424/251; 260/256.4 C; 260/256.4 R; 260/283 CN; 260/287 K; 260/283 S; 4/288 R
[51] Int. Cl.² ............... C07D 239/24
[58] Field of Search ............ 260/256.4 R, 256.4 C; 424/251

[56] References Cited
UNITED STATES PATENTS

2,359,329  10/1944  Phillips ............ 260/287 R
3,544,577  12/1970  Seeger ............. 260/287 R

OTHER PUBLICATIONS

Klingsberg, "Heterocyclic Compounds", 1960, pp. 365–376.

*Primary Examiner*—Donald G. Daus
*Assistant Examiner*—James H. Turnipseed

[57] ABSTRACT

2-Amino-1,4-dihydropyridines bearing a carbonyl function in the 5-position and being optionally substituted by lower alkyl or phenyl in the 6-position, and the corresponding 2-amino-1,4,5,6,7,8-hexahydro-5-oxoquinolines, which derivatives are further substituted by a carbonyl group in the 3-position and optionally substituted in the 4-position by lower alkyl, phenyl, substituted phenyl or a heterocyclic group are antihypertensive agents and coronary vessel dilators. The compounds, of which 2-amino-6-methyl-4-(3-nitrophenyl)-1,4-dihydropyridine-3,5-dicarboxylic acid 3,5-diethyl ester is a representative embodiment, are prepared through condensation of an ylideneacetoacetic acid ester and an amidine.

4 Claims, No Drawings
}

2-AMINO-4-PYRIMIDYL-1,4-DIHYDROPYRIDINE DERIVATIVES

CROSS REFERENCE

This is a division of Ser. No. 438,603 filed Feb. 1, 1974, now U.S. Pat. No. 3,929,798 which in turn is a division of Ser. No. 336,639, filed Feb. 28, 1973, now U.S. Pat. No. 3,867,393.

DETAILED DESCRIPTION

The present invention pertains to 2-amino-1,4-dihydropyridine derivatives, to processes for their production and use and to pharmaceutical compositions containing such compounds and useful as antihypertensive agents and coronary vessel dilators.

In particular, the present invention pertains to compounds of the formula

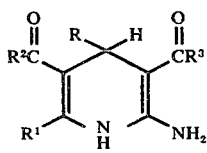

wherein
  R is hydrogen; lower alkyl; lower alkenyl; lower alkynyl; phenyl; substituted phenyl in which the substituents are one to three members selected from the group consisting of lower alkyl, lower alkoxy, halogeno, nitro, cyano, trifluoromethyl, azido, carbo (lower alkoxy), lower alkylsulfonyl, lower alkylsulfinyl, lower alkylthio or phenyl; naphthyl; or a heterocyclic ring selected from the group consisting of quinolyl, isoquinolyl, pyridly, pyrimidyl, thenyl, furyl and pyrryl, said heterocyclic ring being unsubstituted or substituted by one or two members selected from the group consisting of lower alkyl, lower alkoxy and halogeno;
  $R^1$, when taken independently, is hydrogen, lower alkyl, phenyl or pyridly;
  $R^2$, when taken independently, is lower alkyl, lower alkoxy, lower alkoxy (lower alkoxy), lower alkenyloxy, lower alkynyloxy, amino, lower alkylamino or di(lower alkyl)amino,
  $R^1$ and $R^2$ when taken together are alkylene of 2 to 4 carbon atoms; and
  $R^3$ is lower alkyl, lower alkoxy, lower alkoxy (lower alkoxy), lower alkenyloxy, lower alkynyloxy, amino, lower alkylamino or di(lower alkyl)amino.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

The term lower alkoxy denotes a straight or branched hydrocarbon chain bound to the remainder of the molecule through a ethereal oxygen atom as, for example, methoxy, ethoxy, propoxy, isopropoxy, burtoxy, isobutoxy, pentoxy and hexoxy.

The term lower alkylthio denotes a branched or striaght hydrocarbon chain bound to the remainder of the molecule through a divalent sulfur as, for example, methylthio, ethylthio, propylthio, isopropylthio, butylthio, and the like.

The term halogen denotes the substituents fluoro, chloro, bromo and iodo.

As indicated, the present invention also pertains to the physiologically acceptable non-toxic axid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting a dicarbonyl compound of the formula:

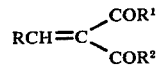

wherein R, $R^1$ and $R^2$ are as herein defined, with an amidine of the formula:

in which $R^3$ is as herein defined. The condensation proceeds smoothly in good yields simply by heating the two components, generally in the presence of an inert organic solvent such as methanol, ethanol, propanol and similar alkanols, ethers such as dioxane and diethyl ehter, glacial acetic acid, pyridine, dimethylformamide, dimethylsulfoxide, acetonitrile and the like. The reaction is conducted at temperatures of from 20 to 250° C, conveniently at the boiling point of the solvent, and while elevated pressure may be utilized, normal atmospheric pressure is generally satisfactory. The reactants are employed in substantially equimolar amounts. The amidine reactant can be employed as the free base or in the form of a salt such as the hydrohalide salts with the amidine being liberated from the salt through treatment with a basic agent such as an alkali metal alkoxide. The dicarbonyl reagent can be utilized as such or generated in situ by the reaction of an aldehyde of the formula RCHO and a β-dicarbonyl compound of the formula $R^1COCH_2COR^2$.

It is rather surprising that the above described condensation produces the desired compounds in such good yields and with such high purity for while it is known that a benzylideneacetoacetic acid ester can be condensed with an amino crotonic acid ester to yield a 1,4-dihydropyridine (Knoevenagel, Ber. 31, 743, 1898), it would be expected from, for example, Silversmith, J. Org. Chem. 27, 4090 (1952) that the addition of an amidine to an α,β-unsaturated keto compound would yield the dihydropyrimidine derivative rather than the dihydropyridine derivative.

Many of the dicarbonyl compounds utilized as one of the reactants are known to the art and the others can either be generated in situ as herein described or prepared according to methods well known to the art, see for example Org. Reaction XV, 204 et seq. (1967). Typical of this reactant are the following compounds:

benzylideneacetoacetic acid methyl ester,
ethylideneacetoacetic acid methyl ester,
isopropylideneacetoacetic acid methyl ester,
2-nitrobenzylideneacetoacetic acid methyl ester,
2-nitrobenzylideneacetylacetone,
benzylideneacetylacetone,
3-nitrobenzylidenecacetoacetic acid methyl ester,
3-nitrobenzylideneacetoacetic acid propargyl ester,
3-nitrobenzylideneacetoacetic acid allyl ester,
3-nitrobenzylideneacetoacetic acid β-methoxyethyl ester,
3-nitrobenzylideneacetoacetic acid β-ethoxyethyl ester,
3-nitrobenzylideneacetoacetic acid isopropyl ester,
3-nitrobenzylideneacetylacetone,
4-nitrobenzylideneacetylacetone,
4-nitrobenzylideneacetoacetic acid β-propoxyethyl ester, 4-nitrobenzylideneacetoacetic acid n-propyl ester,
3-nitro-6-chlorobenzylideneacetoacetic acid methyl ester,
2-cyanobenzylideneacetoacetic acid methyl ester,
2-cyanobenzylideneacetoacetic acid methyl ester,
2-cyanobenzylideneacetoacetic acid ethyl ester,
2-cyanobenzylidenepropionlylacetic acid ethyl ester,
3-cyanobenzylideneacetoacetic acid methyl ester,
3-nitro-4-chlorobenzylideneacetylacetone,
3-nitro-4-chlorobenzylideneacetoacetic acid t-butyl ester,
3-nitro-4-chlorobenzylideneacetoacetic acid methyl ester,
2-nitro-4-methoxybenzylideneacetoacetic acid methyl ester,
2-cyano-4-methylbenzylideneacetoacetic acid ethyl ester,
2-azidobenzylideneacetoacetic acid ethyl ester,
3-azidobenzylideneacetylacetone,
2-methylmercaptobenzylideneacetoacetic acid isopropyl ester,
2-sulphinylmethylbenzylideneacetoacetic acid ethyl ester,
2-sulphonylbenzylidenemethylacetoacetic acid allyl ester,
4-sulphonylmethylbenzylideneacetoacetic acid ethyl ester,
naphth-1-ylideneacetoacetic acid methyl ester,
naphth-1-ylideneacetoacetic acid ethyl ester,
napth-2-ylideneacetoacetic acid ethyl ester,
2-ethoxynaphth-1-ylideneacetoacetic acid methyl ester,
2-methoxynaphth-1-ylideneacetoacetic acid ethyl ester,
5-bromonaphth-1-ylideneacetoacetic acid methyl ester,
quinol-2-ylmethylideneacetoacetic acid methyl ester,
quinol-3-ylmethylideneacetoacetic acid methyl ester,
quinol-4-ylmethylideneacetoacetic acid ethyl ester,
quinol-8-ylemethylideneacetoacetic acid ethyl ester,
isoquinol-1-ylmethylideneacetoacetic acid methyl ester,
isoquinol-3-ylmethylideneacetoacetic acid methyl ester,
α-pyridylmethylideneacetoacetic acid methyl ester,
α-pyridylmethylideneacetoacetic acid ethyl ester,
α-pyridylmethylideneacetoacetic acid allyl ester,
α-pyridylmethylideneacetoacetic acid cyclohexyl ester,
β-pyridylmethylideneacetoacetic acid β-methoxyethyl ester,
γ-pyridylmethyldieneacetoacetic acid methyl ester,
6-methyl-α-pyridylmethylideneacetoacetic acid ethyl ester,
4,6-dimethoxypyrimid-5-ylmethylideneacetoacetic acid ethyl ester,
then-2-ylmethylideneacetoacetic acid ethyl ester,
fur-2-ylmethylideneacetoacetic acid allyl ester,
pyrr-2-ylthylideneacetoacetic acid methyl ester,
nitrobenzylidenepropionylacetic acid ethyl ester,
α-pyridylmethylidenepropionylacetic acid ethyl ester,
α-pyridylmethylidenepropionylacetic acid methyl ester,
α-pyridylmethylideneacetylacetone,
2-, 3- or 4-methoxybenzylideneacetoacetic acid ethyl ester,
2-, 3- or 4-methoxybenzylideneacetylacetone,
2-methoxybenzylideneacetoacetic acid allyl ester,
2-methoxybenzylideneacetoacetic acid allyl ester,
2-methoxybenzylideneacetoacetic acid propargyl ester,
2-methoxybenzylideneacetoacetic acid β-methoxyethyl ester,
2-isopropoxybenzylideneacetoacetic acid ethyl ester,
3-butoxybenzylideneacetoacetic acid methyl ester,
3,4,5-trimethoxybenzylideneacetoacetic acid allyl ester,
2-methylbenzylidenepropionylacetic acid methyl ester,
2-, 3- or 4-methylbenzylideneacetoacetic acid ethyl ester,
2-methylbenzylideneacetoacetic acid β-methoxyethyl ester,
2-methylbenzylideneacetoacetic acid β-propoxyethyl ester,
2-methylbenzylideneacetylacetone,
3,4-dimethoxy-5-bromobenzylideneacetoacetic acid ethyl ester,
2-, 3- or 4-chlorobenzylideneacetoacetic acid ethyl ester,
2-, 3- or 4-bromobenzylideneacetoacetic acid ethyl ester,
2-, 3- or 4-fluorobenzylideneacetoacetic acid ethyl ester,
2-fluorobenzylideneacetoacetic acid methyl ester,
3-chlorobenzylideneacetylacetone,
3-chlorobenzylidenepropinoylacetic acid ethyl ester,
3-chlorobenzylideneacetoacetic acid ethyl ester,
2-chlorobenzylideneacetoacetic acid allyl ester,
2-, 3- or 4-trifluoromethylbenzylideneacetoacetic acid isopropyl ester,
3-trifluoromethylbenzylideneacetoacetic acid methyl ester,
2-carbethoxybenzylideneacetoacetic acid ethyl ester,
3-carbomethoxybenzylideneacetoacetic acid methyl ester,
4-carboisopropoxybenzylideneacetoacetic acid isopropyl ester,
4-carbomethypxybenzylideneacetoacetic acid allyl ester,
3-nitrobenzylidenecyclohexane-1,3-dione, and
3-nitrobenzylidenecycloheptane-1,3-dione.

The amidine reactants are similarly known or can be readily produced according to known methods, see for example McElvain et al., J.A.C.S., 73, 2760 (1951). Typical of these reactants are the following:

amidinoacetic acid methyl ester,
amidinoacetic acid ethyl ester,
amidinoacetic acid n-propyl ester,
amidinoacetic acid isopropyl ester,
amidinoacetic acid cyclohexyl ester,
amidinoacetic acid β-methoxyethyl ester,
amidinoacetic acid α-ethoxyethyl ester,
amidinoacetic acid β-ethoxyethyl ester,
amidinoacetic acid propargyl ester, and
amidinoacetamide.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitritelike effect of reducing the load on the heart. The effect on heart metabolism is thus one of energy saving. In addition, the compounds lower the blood pressure of normotonic and hypertoic animals and can thus be used as antihypertensive agents. These properties can be conveniently observed in well known laboratory models. Thus for example the coronary vessel dilation effect can be observed by measuring the increase in oxygen saturation in the coronary sinus in the narcotized, heart catheterized dog, as shown in the following table:

| Compound | I.V. Dose (mg/kg) | $\Delta O_2\%$ saturation | Return to normal $O_2$ values (hours) |
| --- | --- | --- | --- |
| 2-amino-6-methyl-4-(2-nitrophenyl)-1,4-dihydropyridine-3,5-dicarboxylic acid 3-ethyl-5-methyl ester | 0.02 | 33 | 2.5 |
| 2-amino-6-methyl-4-(2-cyanophenyl)-1,4-dihydropyridine-3,5-dicarboxylic acid diethyl ester | 0.03 | 32 | 3 |
| 2-amino-6-methyl-4-(3-nitrophenyl)-1,4-dihydropyridine-3,5-dicarboxylic acid diethyl ester | 0.01 | 23 | 2 |

The hypotensive activity of the present compounds can be observed by measuring the blood pessure of hypertensive rates following administration of the compounds. The following table demonstrates the dose which results in at least a 15 mm Hg reduction in blood pressure of such animals:

| Compound | Dose (mg/kg) |
| --- | --- |
| 2-amino-6-methyl-4-phenyl-1,4-dihydropyridine-3,5-dicarboxylic acid diethyl ester | 1.0 |
| 2-amino-6-methyl-4-(2-nitrophenyl)-1,4-dihydropyridine-3,5-dicarboxylic acid 3-ethyl ester 5-methyl ester | 0.1 |
| 2-amino-6-methyl-4-(2-methoxyphenyl)-1,4-dihydropyridine-3,5-dicarboxylic acid diethyl ester | 1.0 |
| 2-amino-6-methyl-4-(2-cyanophenyl)-1,4-dihydropyridine-3,5-dicarboxylic acid diethyl ester | 1.0 |
| 2-amino-6-methyl-4-(2-trifluoromethylphenyl)-1,4-dihydropyridine-3,5-dicarboxylic acid diethyl ester | 1.0 |
| 2-amino-6-methyl-4-(3-nitrophenyl)-1,4-dihydropyridine-3,5-dicarboxylic acid diethyl ester | 1.0 |
| 2-amino-6-methyl-4-(3-nitrophenyl)-1,4-dihydropyridine-3,5-dicarboxylic acid 3-ethyl ester 5-methyl ester | 1.0 |
| 2-amino-6-methyl-4-(3-nitrophenyl)-1,4-dihydropyridine-3,5-dicarboxylic acid 3-ethyl ester 5-β-methoxyethyl ester | 1.0 |
| 2-amino-5-acetyl-6-methyl-4-(3-nitrophenyl)-1,4-dihydropyridine-3-carboxylic acid ethyl ester | 3.1 |
| 2-amino-6-methyl-4-(3-nitro-6-chlorophenyl)-1,4-dihydropyridine-3,5-dicarboxylic acid 3-ethyl ester 5-methyl ester | 1.0 |

The toxicity of the compounds is remarkably low. Thus for example the toxic dose of 2-amino-6-methyl-4-(2- trifluoromethylphenyl)-1,4-dihydropyridine-3,5-dicarboxylic acid diethyl ester in mice upon oral administration is greater than 1000 mg/kg.

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5%, of at least one 2-amino-1,4-dihydropyridine as herein defined in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three four or more signal doses or, alternatively, one-half, third or forth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three of four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.001 to about 2 mg/kg, preferably 0.005 to 1.0 mg/kg, when administered parenterally and from about 0.1 to about 20 mg/kg, preferably 0.5 to 10 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions and the like.

Powers are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulatd for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As a alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The midicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral adminstration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of Applicants' invention since the subject matter regarded as the invention is set forth in the appended claims.

EXAMPLE 1

Upon boiling a solution of 21.8 g of benzylideneacetoacetic acid ethyl ester and 13.0 g of amidinoacetic acid ethyl ester in 150 ml of ethanol for 2 hours, 2-amino-6-methyl-4-phenyl-1,4-dihydropyridine-3,5-dicarboxylic acid diethyl ester of melting point 164° C (alcohol) is obtained.

Yield: 67% of theory.

EXAMPLE 2

Upon boiling a solution of 24.9 g of 2-nitrobenzylideneacetoacetic acid methyl ester and 13.0 g of amidinoacetic acid ethyl ester in 100 ml of ethanol for 1 hour, 2-amino-6-methyl-4-(2-nitrophenyl)-1,4-dihydropyridine-3,5-dicarboxylic acid 3-ethyl ester 5-methyl ester of melting point 168° C (alcohol) is obtained.

Yield: 59% of theory.

EXAMPLE 3

Upon boiling a solutin of 24.8 g of 2-methoxybenzylideneacetoacetic acid ethyl ester and 13.0 g of amidinoacetic acid ethyl ester in 150 ml of ethanol for 1 hour, 2-amino-6-methyl-4-(2-methoxyphenyl)-1,4-dihydropyridine-3,5-dicarboxylic acid diethyl ester of melting point 170° C (ethanol) is obtained.

Yield: 65% of theory.

EXAMPLE 4

Upon boiling a solution of 23.2 g of 2-methylbenzylideneacetoacetic acid ethyl ester and 13.0 g of amidinoacetic acid ethyl ester in 150 ml of ethanol for 2 hours, 2-amino-6- methyl-4-(2-methylphenyl)-1,4-dihydropyridine-3,5 -dicarboxylic acid diethyl ester of metling point 130° C (ethanol) is obtained.

Yield: 71% of theory.

EXAMPLE 5

Upon boiling a solution of 24.3 g of 2-cyanobenzylideneacetoacetic acid ethyl ester and 13.0 g of amidinoacetic acid ethyl ester in 100 ml of ethanol for 2 hours, 2-amino-6- methyl-4 -(2-cyanophenyl)-1,4-dihydropyridine-3,5-dicarboxylic acid diethyl ester of melting point 208° C (ethanol) is obtained.

Yield: 54% of theory.

EXAMPLE 6

Upon boiling a solution of 14.2 g of 2-trifluoromethylbenzylideneacetoacetic acid ethyl ester and 6.5 g of amidinoacetic acid ethyl ester in 100 ml of ethanol for 1 hour, 2-amino-6-methyl-4-(2-trifluoromethylphenyl)-1,4-dihydropyridine -3,5-dicarboxylic acid diethyl ester of melting point 156° C (ethanol) is obtained.

Yield: 76% of theory.

EXAMPLE 7

Upon boiling a solution of 12.6 g of 3-chlorobenzylideneacetoacetic acid ethyl ester and 6.5 g of amidinoacetic acid ethyl ester in 100 ml of ethanol for 2 hours, 2-amino-6- methyl-4-(3-chlorophenyl)-1,4-dihydropyridine-3,5-dicarboxylic acid diethyl ester of melting point 157 –   ° C (ethanol) is obtained.

Yield: 62% of theory.

EXAMPLE 8

Upon boiling a solution of 13.2 g of 4-methylmercaptobenzylideneacetoacetic acid ethyl ester and 6.5 g of amidinoacetic acid ethyl ester in 100 ml of ethanol for 1 hour, 2- amino-6-methyl-4-(4-methylmercaptophenyl)-1,4-dihydropyridine- 3,5-dicarboxylic acid diethyl ester of melting point 165° C (ethyl acetate/petroleum ether) is obtained.

Yield: 49% of theory.

EXAMPLE 9

Upon boiling a solution of 26.3 g of 3-nitrobenzylideneacetoacetic acid ethyl ester and 13.0 g of amidinoacetic acid ethyl ester in 200 ml of ethanol for 1 hour, 2-amino-6- methyl-4-(3-nitrophenyl)-1,4-dihydropyridine 3,5-dicarboxylic acid diethyl ester of melting point 169° C (ethanol) is obtained.

Yield: 58% of theory.

EXAMPLE 10

Upon boiling a solution of 24.9 g of 3-nitrobenzylideneacetoacetic acid methyl ester and 13.0 g of amidinoacetic acid ethyl ester in 180 ml of ethanol for 1 hour, 2-amino-6- methyl-4-(3-nitrophenyl)-1,4-dihydropyridine-3,5-dicarboxylic acid 3-ethyl ester 5-methyl ester of melting point 124° C is obtained.

Yield: 59% of theory.

EXAMPLE 11

Upon heating a solution of 13.8 g of 3-nitrobenzylideneacetoacetic acid isopropyl ester and 6.5 g of amidinoacetic acid ethyl ester in 150 ml of ethanol for 2 hours, 2-amino-6- methyl-4-(3-nitrophenyl)-1,4-dihydropyridine-3,5-dicarboxylic acid 3-ethyl 5-isopropyl ester of melting point 206 – 207° C (alcohol) is obtained.

Yield: 62% of theory.

EXAMPLE 12

Boiling a solution of 10.9 g of 3-nitrobenzylideneacetoacetic acid propargyl ester and 5.2 g of amidinoacetic acid ethyl ester in 100 ml of ethanol for 1 hour yields 2- amino-6-methyl-4-(3-nitrophenyl)-1,4-dihydropyridine-3,5- dicarboxylic acid 3-ethyl ester 5-propargyl ester of melting point 181° C (ethanol).

Yield: 59% of theory.

EXAMPLE 13

Heating a solution of 14.6 g of 3-nitrobenzylideneacetoacetic acid β-methaoxyethyl ester and 6.5 g of amidinoacetic acid ethyl ester in 150 ml of ethanol for 1 hour yields 2-amino-6-methyl-4-(3-nitrophenyl)-1,4-dihydropyridine-3,5- dicarboxylic acid 3-ethyl ester 5β-methoxyethyl ester of melting point 179° C (ethyl acetate/petroleum ether).

Yield: 58% of theory.

EXAMPLE 14

Upon boiling a solution of 7.6 g of 3-nitrobenzaldehyde, 5.0 g of acetylacetone and 6.5 g of amidinoacetic acid ethyl ester in 100 ml of ethanol for 2 hours, 2-amino-5-acetyl- 6-methyl-4-(3-nitrophenyl)-1,4-dihydropyridine-3-carboxylic acid ethyl ester of melting point 217° C (ethanol) is obtained.

Yield: 48% of theory.

EXAMPLE 15

Upon boiling a solution of 14.2 g of 3-nitro-6- chlorobenzylideneacetoacetic acid methyl ester and 6.5 g of amidinoacetic acid ethyl ester in 100 ml of ethanol for 1 hour, 2-amino-6-methyl-4-(3-nitro-6-chlorophenyl)-1,4-dihydropyridne- 3,5-dicarboxylic acid 3-ethyl ester 5-methyl ester of melting point 124° C (ethanol) is obtained.

Yield: 73% of theory.

EXAMPLE 16

Upon boiling a solution of 10.4 g of 2-furfurylideneacetoacetic acid ethyl ester and 6.5 g of amidinoacetic acid ethyl ester in 100 ml of ethanol for 2 hours, 2-amino-6-methyl- 4-(fur-2-yl)-1,4-dihydropyridine-3,5-dicarboxylic acid diethyl ester of melting point 183° C (isopropanol) is obtained.

Yield: 78% of theory.

EXAMPLE 17

Upon boiling a solution of 14.0 g of benzoylacetic acid ethyl ester and 6.5 g of amidinoacetic acid ethyl ester in 150 ml of ethanol for 2 hours, 2-amino-4,6-diphenyl-1,4-dihydropyridine-3,5-dicarboxylic   acid ethyl ester of melting point 183° C (ethanol) is obtained.

Yield: 48% of theory.

EXAMPLE 18

Upon heating a solution of 15.6 g of ethylideneacetoacetic acid ethyl ester and 13.0 g of amidinoacetic acid ethyl ester in 100 ml of ethanol for 2 hours, 2-amino-4,6-dimethyl- 1,4-dihydropyridine-3,5-dicarboxylic acid diethyl ester of melting point 140° C (isopropanol) is obtained.

Yield: 59% of theory.

dihydropyridine-3,5-dicarboxylic acid diisopropyl ester of melting point 122° C (ether) is obtained.

Yield: 62% of theory.

EXAMPLE 34

Upon boiling a solution of 12.2 g of 2-cyanobenzylideneacetoacetic acid ethyl ester and 7.2 g of amidinoacetic acid isopropyl ester in 200 ml of ethanol for 1 hour, 2-amino- 6-methyl-4-(2-cyanophenyl)-1,4-dihydropyridine-3,5-dicarboxylic acid 3-isopropyl esrter 5-ethyl ester of melting point 200° C (isopropanol) is obtained.

Yield: 58% of theory.

EXAMPLE 35

Upon heating a solution of 12.5 g of 3-nitrobenzylideneacetoacetic acid methyl ester and 7.2 g of amidinoacetic acid isopropyl ester in 150 ml of ethanol for 2 hours, 2-amino- 6-methyl-4-(3-nitrophenyl)-1,4-dihydropyridine-3,5-dicarboxylic acid 3-isopropyl ester 5-methyl ester of melting point 167° C (ethanol) is obtained.

Yield: 82% of theory.

EXAMPLE 36

Upon heating a solution of 11.0 g of 2-trifluoromethyl -4-nitrobenzaldehyde, 5.6 g of cyclohexane-1,3-dione and 6.5 g of amidinoacetic acid ethyl ester in 250 ml of ethanol of 2 hours, 2-amino-4-(2-trifluoromethyl-4-nitrophenyl)- 1,4,5,6,7,8-hexahydro-5-oxoquinoline-3-carboxylic acid ethyl ester of melting point 264° C (ethanol) is obtained.

Yield: 62% of theory.

EXAMPLE 37

Heating a solution of 13.2 g of 3-nitrobenzylideneacetoacetic acid ethyl ester and 7.2 g of amidinoacetic acid n-propyl ester in 200 ml of ethanol for 2 hours yields 2-amino- 6-methyl-4-(3-nitrophenyl)-1,4-dihydropyridine-3,5-dicarboxylic acid 3-n-propyl ester 5-ethyl ester of melting point 168° C (ethanol).

Yield: 79% of theory.

EXAMPLE 38

Boiling a solution of 8.5 g of 6-nitroveratraldehyde, 4.0 g of cyclohexane-1,3-dione and 5.2 g of amidinoacetic acid ethyl ester in 150 ml of ethanol for 1 hour yields 2-amino-4- (2-nitro-4,5-dimethoxyphenyl)-1,4,5,6,7,8-hexahydro-5-oxoquinoline -3-carboxylic acid ethyl ester of melting point 261° C (ethanol).

Yield: 52% of theory.

EXAMPLE 39

Boiling a solution of 13.2 g of 3-nitrobenzylideneacetoacetic acid ethyl ester and 8.0 g of amidinoacetic acid β-methoxyethyl ester in 200 ml of ethanol for 2 hours yields 2-amino-6-methyl-4-(3-nitrophenyl-1,4-dihydropyridine-3,5- dicarboxylic acid 3-(β-methoxyethyl) ester 5-ethyl ester of melting point 174° C.

Yield: 59% of theory.

EXAMPLE 40

Upon heating a solution of 6.1 g of biphenyl-2- aldehyde, 3.8 g of cyclohexane-1,3-dione and 5.1 g of amidinoacetic acid ethyl ester in 100 ml of ethanol for 1 hour, 2- amino-4-(biphenyl-2-yl)-1,4,5,6,7,8-hexahydro-5-oxoquinoline- 3-carboxylic acid ethyl ester of melting point 248° C (ethanol) is obtained.

Yield: 45% of theory.

EXAMPLE 41

Boiling a solution of 13.4 g of (1-naphthylidene)-acetoacetic acid ethyl ester and 6.5 g of amidinoacetic acid ethyl ester in 100 ml of ethanol for 8 hours yields 2-amino-6-methyl-4-(1-naphthyl-1,4-dihydropyridine-3,5-dicarboxylic acid diethyl ester of melting point 174° C (ethanol).

Yield: 62% of theory.

EXAMPLE 42

Upon heating a solution of 11.5 g of 2-cyanobenzyldeneacetoacetic acid methyl ester and 7.2 g of amidinoacetic acid isopropyl ester in 100 ml of ethanol for 6 hours, 2-amino-6-methyl-4-(2-cyanophenyl)-1,4-dihydropyridine-3,5-dicarboxylic acid 3-isopropyl ester 5-methyl ester of melting point 211° C (ethanol) is obtained. Yield: 72% of theory.

EXAMPLE 43

Upon boiling a solution of 11.5 g of 2-cyonobenzylideneacetoacetic acid methyl ester and 6.5 g of amidinoacetic acid ethyl ester in 100 ml of ethanol for 8 hours, 2-amino-6-methyl-4-(2-cyanophenyl-)-1,4-dihydropyridine-3,5-dihydropyridine-3,5-dicarboxylic acid 3-ethyl ester 5-methyl ester of melting point 224° C (ethanol) is obtained. Yield: 66% of theory.

EXAMPLE 44

Upon boiling a solution of 14.8 g of 2-phenylbenzylideneacetoacetic acid ethyl ester and 6.5 g of amidinoacetic acid ethyl ester in 100 ml of ethanol for 8 hours, 2-amino-6-methyl-4-(biphenyl-2-yl) -1,4-dihydropyridine-3,5-dicarboxylic acid ethyl ester of melting point 182° (ethanol) is obtained. Yield: 41% of theory.

EXAMPLE 45

Upon heating a solution of 12.5 g of 3-nitrobenzylideneacetoacetic acid methyl ester and 7.2 g of amidinoacetic acid n-propyl ester in 100 ml of ethanol for 6 hours, 2-amino-6-methyl-4-(3-nitrophenyl)-1,4-dihydropyrindine-3,5 dicarboxylic acid 3-n-propyl ester 5-methyl ester of melting point 155° C (ethanol) is obtained. Yield: 69% of theory.

EXAMPLE 46

Upon heating a solution of 12.2 g of (2-thenylidene)-acetoacetic acid ethyl ester and 6.5 g of amidinoacetic acid ethyl ester in 100 ml of ethanol for 4 hours, 2-amino-6-methyl-4-(2thenyl)-1,4-dihydropyridine-3,5-dicarboxylic acid diethyl ester of melting point 170° C (ethanol) is obtained. Yield: 73% of theory.

EXAMPLE 47

Upon heating a solution of 10.9 g of benzylideneacetoacetic acid diemethylamide and 5.0 g of amidinoacetamide in 100 ml of ethanol for 8 hours, 2-amino-6-methyl-4-phenyl-5-(N,N-dimethylaminocarbonyl)-1,4-dihydropyridine-3-carboxylic acid amide of melting point 236° C (ethanol) is obtained. Yield: 50% of theory.

EXAMPLE 48

Heating a solution of 10.9 g of benzylideneacetoacetic acid dimethylamide and 6.5 g of amidinoacetic acid ethyl ester in 100 ml of methanol for 6 hours yields 2-amino-6-methyl-4-phenyl-1,4-dihydropyridine-3,5-dicarboxylic acid 3-ethyl ester 5-(N,N-dimethylamide) of melting point 230° C (alcohol). Yield: 61% of theory.

EXAMPLE 49

Boiling a solution of 13.2 g of 2-nitrobenzylideneacetoacetic acid ethyl ester and 7.2 g of amidinoacetic acid isopropyl ester in 100 ml of ethanol for 6 hours yields 2-amino-6-methyl-4-(2-nitrophenyl)-1,4-dihydropyridine-3,5-dicarboxylic acid 3-isopropyl ester 5-ethyl ester of melting pont 139° C (isopropanol). Yield: 39% of theory.

EXAMPLE 50

Boiling a solution of 13.2 g of 2-nitrobenzylideneacetoacetic acid ethyl ester and 6.5 g of amidinoacetic acid ethyl ester in 100 ml of ethanol for 6 hours yields 2-amino-6-methyl-4-(2-nitrophenyl)-1,4-dihydropyridine-3,5-dicarboxylic acid diethyl ester of melting point 159° C (ethanol). Yield: 52% of theory.

EXAMPLE 51

Upon heating a solution of 12.5 g of 2-nitrobenzylideneacetoacetic acid methyl ester and 7.2 g of amidinoacetic acid isopropyl ester in 100 ml of ethanol for 8 hours, 2-amino-6-methyl-4-(2 -nitrophenyl)-1,4-dihydropyridien-3,5-dicarboxylic acid 3-isopropyl ester 5-methyl ester of melting point 203° C (isopropanol) is obtained. Yield: 50% of theory.

EXAMPLE 52

Upon heating a solution of 12.2 g of 2-cyanobenzylideneacetoacetic acid ethyl ester and 7.2 g of amidinoacetic acid n-propyl ester in 100 ml of ethanol for 8 hours, 2-amino-6-methyl-4-(2-cyanophenyl)-1,4-dihydropyridine-3,5-dicarboxylic acid 3-n-propyl ester 5-ester of melting point 182° C (ethanol) is obtained. Yield: 62% of theory.

EXAMPLE 53

Upon heating a solution of 13.9 g of 3-nitrobenzylideneacetoacetic acid isopropyl ester and 7.2 g of amidinoacetic acid n-propyl ester in 100 ml of ethanol for 6 hours, 2-amino-6-methyl-4-(3-nitrophenyl)-1,4-dihydropyridine-3,5-dicarboxylic acid 3-n-propyl ester 5-isopropyl ester of melting point 199° C (isopropanol) is obtained. Yield: 75% of theory.

EXAMPLE 54

Heating a solution of 6.5 g of 3-cyanobenzaldehyde, 5.6 g of cyclohexane-1,3-dione and 6.5 g of amidinoacetic acid ethyl ester in 100 ml of ethanol for 6 hours yields 2-amino-4-(3-cyanophenyl)-1,4,5,6,7,8-hexahydro-5-oxoquinoline-3-carboxylic acid ethyl ester of melting point 262° C (ethanol/dimethylformamide). Yield: 56% of theory.

EXAMPLE 55

Upon heating a solution of 9.3 g of 3-bromobenzaldehyde, 5.6 g of cyclohexane-1,3-dione and 6.5 g of amidinoacetic acid ethyl ester in 100 ml of ethanol for 8 hours, 2-amino-4-(3-bromophenyl-1,4,5,6,7,8-hexahydro-5-oxoquinoline-3-carboxylic acid ethyl ester of melting point 255° C (ethanol) is obtained. Yield: 44% of theory.

EXAMPLE 56

Upon boiling a solution of 9.3 g of 3-bromobenzaldehyde, 5.6 g of cyclohexane-1,3-dione and 6.5 g of amidinoacetic acid ethyl ester in 100 ml of ethanol for 6 hours. 2-amino-4-(2-bromophenyl)-1,4,5,6,7,8-hexahydro-5-oxoquinoline-3-carboxylic acid ethyl ester of melting point 245° C (ethanol) is obtained. Yield: 46% of theory.

EXAMPLE 57

Upon heating a solution of 8.9 g of 3-carbethoxybenzaldehyde, 5.6 g of cyclohexane-1,3-dione and 6.5 g of amidinoacetic acid ethyl ester in 100 ml of ethanol for 4 hours, 2-amino-4-(3-carbethoxyphenyl)-1,4,5,6,7,8-hexahydro-5-oxoquinoline-3-carboxylic acid ethyl ester of melting point 234° C (ethanol) is obtained. Yield: 54% of theory.

EXAMPLE 58

Upon heating a solution of 7.4 of 2-azidobenzaldehyde, 5.6 g of cyclohexane-1,3-dione and 6.5 g of amidinoactic acid ethyl ester in 100 ml of ethanol for 4 hours, 2-amino-4-(2-azidophenyl)-1,4,5,6,7,8-hexahydro-5-oxoquinoline-3carboxylic acid ethyl ester of melting point 209° C (ethanol) is obtained. Yield: 58% of theory.

We claim:
1. A compound of the formula:

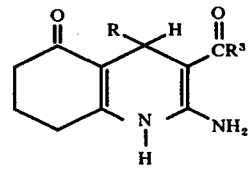

wherein
R is pyrimidyl, unsubstituted or substituted by one or two members selected from the group consisting of lower alkyl, lower alkoxy and halogeno; and
$R^3$ is lower alkoxy or lower alkoxy (lower alkoxy).
2. The compound according to claim 1 which is 2-amino-4-(4,6-dimethoxypyrimid-5-yl)-1,4,5,6,7,8-hexahydro-5-oxoquinoline-3-carboxylic acid ethyl ester.
3. The method of effecting coronary vessel dilation and a reduction in blood pressure in an animal which comprises administering thereto an effective amount of a compound according to claim 1.
4. A pharmaceutical composition for use in effecting coronary vessel dilation and a reduction in blood pressure which comprises an effective amount of a compound according to claim 1 and a pharmaceutical carrier.

* * * * *